United States Patent
Seibold et al.

(10) Patent No.: US 9,226,795 B2
(45) Date of Patent: Jan. 5, 2016

(54) ROBOT STRUCTURE

(75) Inventors: Ulrich Seibold, Burnaby (CA);
Bernhard Kuebler, Oedheim (DE);
Sophie Lantermann, Munich (DE);
Ulrich Hagn, Paehl (DE)

(73) Assignee: DEUTSCHES ZENTRUM FUER LUFT-UND RAUMFAHRT E.V., Cologne (DE)

( * ) Notice: Subject to any disclaimer, the term of this patent is extended or adjusted under 35 U.S.C. 154(b) by 448 days.

(21) Appl. No.: 13/808,871

(22) PCT Filed: Jun. 16, 2011

(86) PCT No.: PCT/EP2011/060054
§ 371 (c)(1),
(2), (4) Date: Jan. 14, 2013

(87) PCT Pub. No.: WO2012/004109
PCT Pub. Date: Feb. 12, 2012

(65) Prior Publication Data
US 2013/0116707 A1    May 9, 2013

(30) Foreign Application Priority Data
Jul. 6, 2010   (DE) .......................... 10 2010 026 305

(51) Int. Cl.
*A61B 19/00* (2006.01)
*A61B 17/29* (2006.01)
*B25J 15/02* (2006.01)
*A61B 17/3201* (2006.01)
*A61B 17/00* (2006.01)

(52) U.S. Cl.
CPC ............. *A61B 19/2203* (2013.01); *A61B 17/29* (2013.01); *B25J 15/022* (2013.01);
(Continued)

(58) Field of Classification Search
CPC ............... A61B 17/29; A61B 17/3201; A61B 19/2203; A61B 2019/464; B25J 15/022
USPC .......................................... 606/205–209, 130
See application file for complete search history.

(56) References Cited

U.S. PATENT DOCUMENTS

2008/0147090 A1*  6/2008  Seibold et al. ................ 606/130
2008/0276746 A1   11/2008  Seibold

FOREIGN PATENT DOCUMENTS

DE    10 2006 059 952 B3    6/2008
DE    10 2007 022 122 A1    11/2008
WO        00/51486 A1       9/2000

OTHER PUBLICATIONS

Written Opinion and International Search Report dated Sep. 22, 2011, as issued in corresponding International Application No. PCT/EP2011/060054, filed Jun. 16, 2011 (English translation not available).

(Continued)

*Primary Examiner* — Kathleen Holwerda
(74) *Attorney, Agent, or Firm* — Maier & Maier, PLLC

(57) ABSTRACT

A robot structure, in particular for minimally invasive surgery, is provided with a first robot element and a second robot element that can be moved relative to the first robot element, said second robot element having two grasping and/or cutting elements which can be uniformly moved with respect to each other and which are connected to the first robot element via a hinge axis. The robot structure further has a force transmitting device for moving the grasping and/or cutting elements of the movable robot element and at least one sensor element comprising a sensitive end for receiving forces and/or torques that occur on the movable robot element and includes a base element that is fixed to the first robot element.

20 Claims, 2 Drawing Sheets

Figure 1:
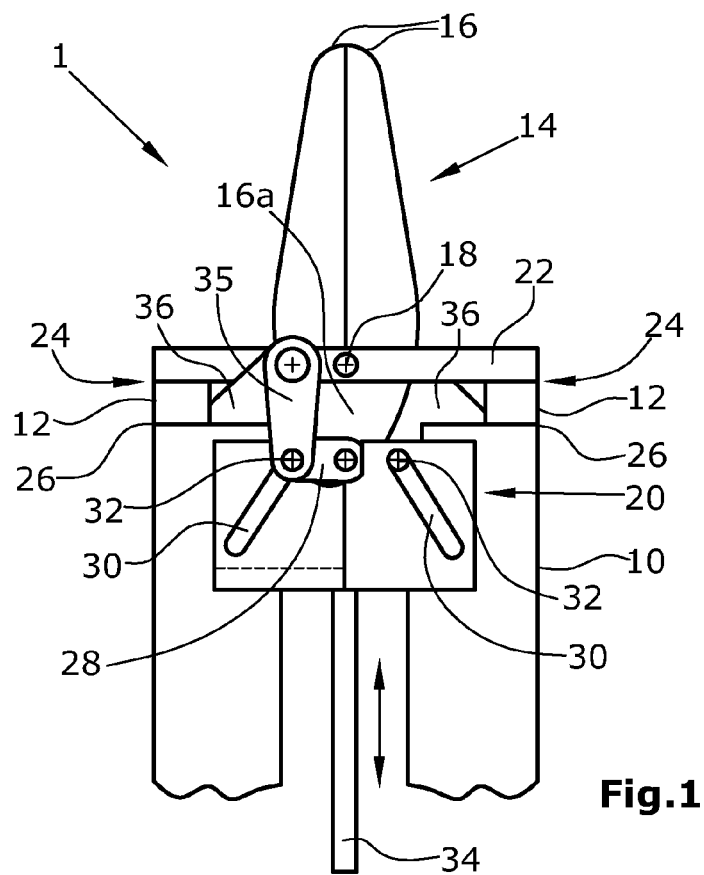

(52) U.S. Cl.
CPC ... *A61B17/3201* (2013.01); *A61B 2017/00367* (2013.01); *A61B 2017/2936* (2013.01); *A61B 2017/2939* (2013.01); *A61B 2019/464* (2013.01)

(56) References Cited

OTHER PUBLICATIONS

Jacob Rosen, et al., "Force Controlled and Teleoperated Endoscopic Grasper for Minimally Invasive Surgery—Experimental Performance Evaluation", IEEE Transactions on Biomedical Engineering, vol. 46, No. 10, pp. 1212-1221, Oct. 1999.

Gregory Tholey, et al., "Design, Development, and Testing of an Automated Lapaoscopic Grasper with 3-D Force Measurement Capability", Medical Simulation: International Symposium, ISMS 2004.

H. Mayer, et al., "Upgrading Instruments for Robotic Surgery", Australian Conference on Robotics & Automation, 2004.

\* cited by examiner

ROBOT STRUCTURE

RELATED APPLICATIONS

This application is the U.S. national stage application which claims priority under 35U.S.C. §371 to International Patent Application No.: PCTIEP2011/060054, filed on Jun. 16, 2011, which claims priority under 35 U.S.C. §119 to German Patent Application No. 10 2010 026 305.2, filed on Jul. 6, 2010, the disclosures of which are incorporated by reference herein their entireties.

The invention refers to a robot structure, in particular for minimally invasive surgery.

In robot-assisted minimally invasive surgery instruments such as grasping and cutting instruments are provided at the distal end of a robot structure. During surgery, the instruments are inside a patient's body. In order to be able to actuate and move the instruments connected with the robot structure, the robot structure comprises at least two robot elements coupled via one joint or a plurality of joints. In this case, a first robot element is designed as a robot arm, for instance, and the second, movable robot element is configured as a grasper or scissors mechanism. For the actuation of the movable robot element, the same is connected with a force transmission means.

For the measuring of the forces occurring, in particular the contact and grasping forces, the robot structure is connected with a sensor element. In this context, there is a general problem that the contact forces and the grasping forces of the movable robot element can be measured only with a rather poor resolution, since the forces occurring are superimposed by rather great driving or movement forces exerted by the force transmission means on the movable robot element. Here, grasping forces are the forces that occur when an object is grasped which is not in contact with the surrounding. Contact forces occur due to the interaction of an instrument or a grasped object with the surrounding. Contact forces are independent of the grasping condition. Contact forces have six degrees of freedom, i.e., three forces and three moments.

For the measuring of the grasping force it is known, for example, to measure the driving or movement force. Here, the driving force is a measure of the grasping force and thus has no interfering influences. However, measuring the grasping force is rather imprecise. Such an instrument is described in J. Rosen, B. Hannaford, M. MacFarlane and M. Sinanan, "Force Controlled and Teleoperated Endoscopic Grasper for Minimally Invasive Surgery—Experimental Performance Evaluation", IEEE Transactions on Biomedical Engineering, 1999, and G. Tholey, A. Pillarisetti, W. Green and J. Desai, "Design, Development and Testing of an Automated Laparoscopic Grasper with 3D Force Measurement Capability", Medical Simulation: International Symposium, ISMS 2004.

Further, it is known for a measurement of the forces occurring, to provide corresponding sensors in the grasping jaws, such as pressure sensors, for example. However, this instrument described in G. Tholey, A. Pillarisetti, W. Green and J. Desai, "Design, Development and Testing of an Automated Laparoscopic Grasper with 3D Force Measurement Capability", Medical Simulation: International Symposium, ISMS 2004 has the disadvantage that only little installation space is available for the integration of sensors, since the grasping jaws must be as small as possible, especially for minimally invasive surgery.

Further, H. Mayr, I. Nagy, A Knoll, E. Schirmbeck and R. Bauernschmitt, "Up-grading Instruments for Robotic Surgery", Australasian Conference on Robotics & Automation, 2004, describes an instrument provided with Bowden cables for the transmission of driving forces by means of a pulling means. Here, the forces are supported using a rigid sleeve that is flexible but has a tensile stiffness in the axial direction. Here, the sleeve serves both to close the force flow of the driving forces, which are rather great forces, and to measure the contact forces which are comparatively small. The Bowden cables support at least a part of the axial forces to be measured.

This entails a deterioration of the measuring results. The influence of the support depends on the position of the Bowden cables with respect to the sensor. Thus, the influence on the support may vary and cannot or only insufficiently be compensated for mathematically.

Even if constructed skillfully, the driving forces transmitted by the Bowden cables at least partly superimpose the contact forces. Among other reasons, this effect is caused by the sleeve of the Bowden cable inevitably expanding or shortening when axial tensile or pressure forces occur, whereby it is impossible to avoid the induction of undesirable driving forces.

From the applicant's DE 10 2006 059 952, a robot structure is known in which grasping elements of a robot element are driven by means of cable pulls. The driving forces may be supported at the base of the sensor and are thus not included in the measuring result.

A solution based on cable pulls, however, starts from a largely friction- and loss-free transmission of forces and a corresponding guiding of the cables. Due to manufacturing tolerances and material properties, these preconditions cannot or only with great effort be fulfilled, given the high degree of miniaturization of the instrument that is desirable for minimally invasive surgery, for instance. This makes the manufacture and the assembly of the mechanics of such instruments very intricate and costly. Further, cable pulls used as driving elements are sterilizable only to a limited extent so that such instruments are only of limited applicability in minimally invasive surgery.

DE 10 2007 022 122 A1 discloses a surgical robot arrangement in which the driving force can also be supported at the base of the sensor, the robot arrangement implementing a hydraulic drive principle. In minimally invasive surgery, however, the use of hydraulic components is often undesirable.

It is an object of the present invention to provide a robot structure with which the grasping and contact forces of the grasping or cutting instruments can be measured with high accuracy and the disadvantages of the prior art are avoided. Here, a further miniaturization of the robot structure and a good sterilizability of the driving elements should be achieved, if possible.

The object is achieved with the features of claim 1.

According to the invention a robot structure, in particular for use in minimally invasive surgery, is provided which comprises a first robot element and a second robot element movable relative thereto, which second robot element comprises two grasping and/or cutting elements which can be uniformly moved with respect to each other and which are connected to the first robot element via a hinge axis. The robot structure further has a transmitting device for moving the grasping and/or cutting elements of the movable robot element and at least one sensor element comprising a sensitive end for receiving forces and/or moments that occur on the movable robot element and comprising a base element that is fixed to the first robot element. The hinge axis is supported in a support element in order to receive the forces and/or moments that are caused by grasping and/or contact forces on the grasping and/or cutting elements, and the support element is connected to the sensitive end of each sensor element. The force-transmitting device is connected to one of the grasping and/or cutting elements via a driving element, respectively, in order to initiate the movement, with the driving elements being disposed opposed to each other and orthogonally or in a substantially orthogonal manner with respect to the central axis of the robot structure and remaining in the orthogonal arrangement with respect to the central axis during the entire moving process of the grasping and/or cutting elements.

By arranging the driving elements orthogonally to the central axis of the robot structure and opposed to each other, the forces exerted by the driving elements on the grasping and/or cutting elements are also induced into the grasping and/or cutting elements exclusively, or at least for the greater part, in a direction orthogonal with respect to the central axis. The driving forces superimpose each other at the hinge axis and in the support element, with the driving forces at the hinge axis also being opposed with respect to each other due to the mutually opposed arrangement of the driving elements, so that they cancel each other at least for the greater part. It is avoided, or at least largely avoided, thereby that force components applied by the driving elements onto the grasping and/or cutting elements are transmitted to the sensitive ends of the sensor elements via the support element. Thus, the driving force is not included in the measuring result measured by the sensor elements so that a very precise determination of the grasping and/or contact forces is possible.

The driving elements may be designed as rods, for example. A rod allows for an advantageous force transmission to the grasping and/or cutting elements, while the rod can be held in the orthogonal arrangement with respect to the central axis of the robot structure, using means of simple structure. Driving elements in the form of rods make it possible to advantageously induce mutually opposed tensile and pressure forces into the grasping and/or cutting elements in a direction orthogonal to the central axis of the robot structure so that the force components cancel each other in the hinge axis.

The force transmitting device may comprise guide elements, for example, with a respective guide element guiding a driving element such that each guide element remains in the orthogonal arrangement with respect to the central axis throughout the movement of the grasping and/or cutting element.

In this instance, the guide elements may be designed as guide levers, for example. In this manner, it is ensured in a structurally simple manner that the driving elements are always arranged in the orthogonal arrangement with respect to the central axis of the robot structure.

It may be provided that the guide elements are respectively connected with the first robot element and/or the base element of one of the sensor elements, preferably via a connecting element. Such a structure allows axial forces exerted by the force transmitting device on the guide elements to be transmitted to the first robot element and/or the base elements of the sensor elements via the connecting elements. It is thereby avoided that the axial forces are transmitted to the support element and thus to the sensitive ends of the sensor elements via the driving elements, the grasping and/or cutting elements and the hinge axis. Thus, axial forces of the force transmitting device are not included in the measuring result so that a very exact measuring of the grasping and/or contact forces is possible.

According to an embodiment of the invention, the force transmitting device comprises a slotted guide device for each driving element, which drives a respective driving element. Each driving element preferably comprises a pin guided in the slotted guide device. Such an arrangement can be obtained in a structurally simple manner, with a good sterilizability being provided due to the simple mechanical design.

The slotted guide devices may each comprise a guiding groove arranged under an angle with respect to the central axis of the robot structure. Such a guiding groove makes it possible to advantageously transmit the driving force from the force transmitting device to the guide elements and the driving elements, it being possible, by a movement of the force transmitting device in the axial direction of the robot structure, to generate a force in the driving elements that acts in a direction orthogonal to the central axis of the robot structure. Thereby, it is possible to generate the desired driving force in the driving elements by a simple movement of the force transmitting device in the axial direction of the robot structure.

In an alternative embodiment of the invention, the force transmitting device drives the driving elements via levers.

It may be provided that the force transmission device can be driven via a pull/push rod. Depending on the structural design of the present robot structure, a corresponding opening or closing of the grasping and/or cutting elements is possible through a pulling or pushing movement of the pull/push rod and thus of the force transmission device.

As an alternative, the force transmitting device may be adapted to be driven by means of a pull rod or a push rod, the pull rod or the push rod preferably being spring-biased. The spring bias ensures that after the induction of a movement, for instance a closing of the grasping and/or cutting elements, into the force transmitting device, this movement is carried out against the spring bias, and that the grasping and/or cutting elements are returned to the open position under the action of the spring bias.

According to an embodiment of the invention it may also be provided that the force transmitting device can be driven by a pull cable, the pull cable preferably being spring-biased.

Figure 2:
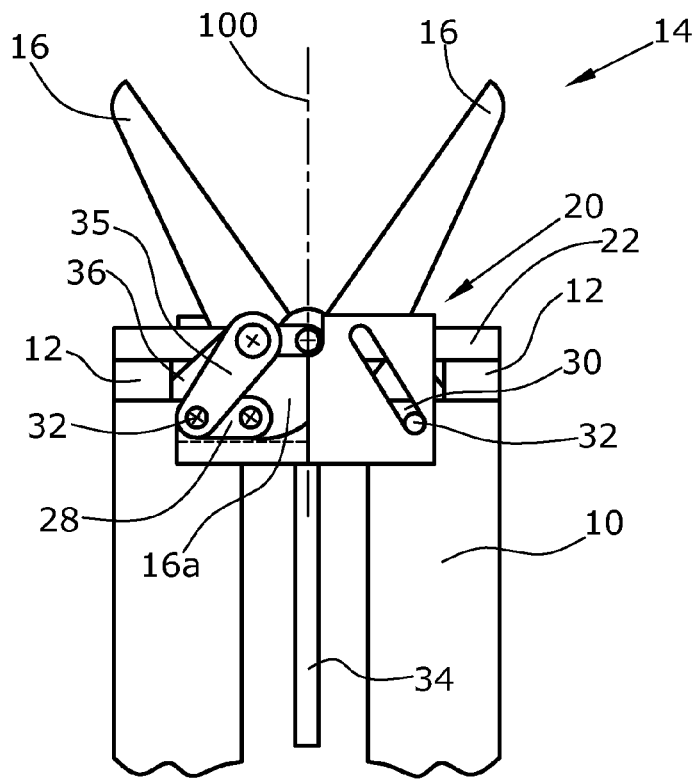
Figure 3:
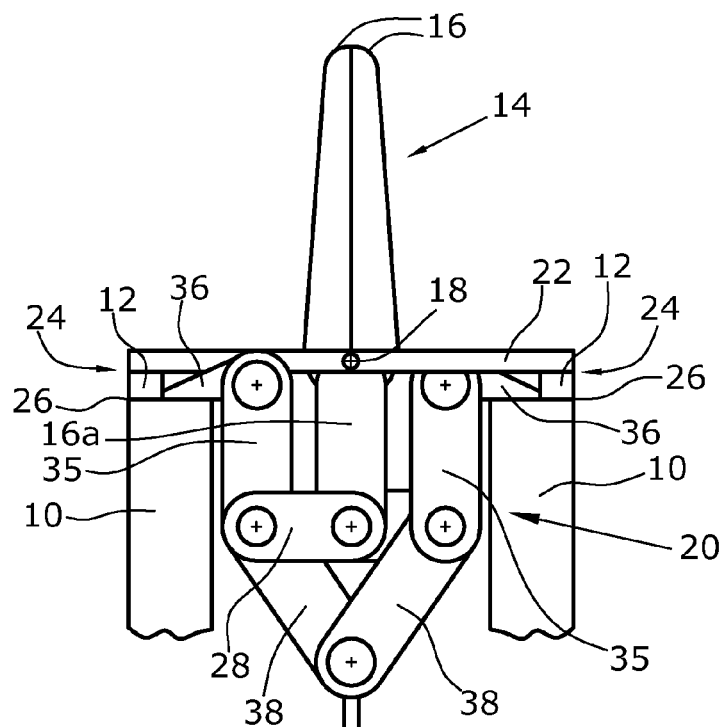
Figure 4:
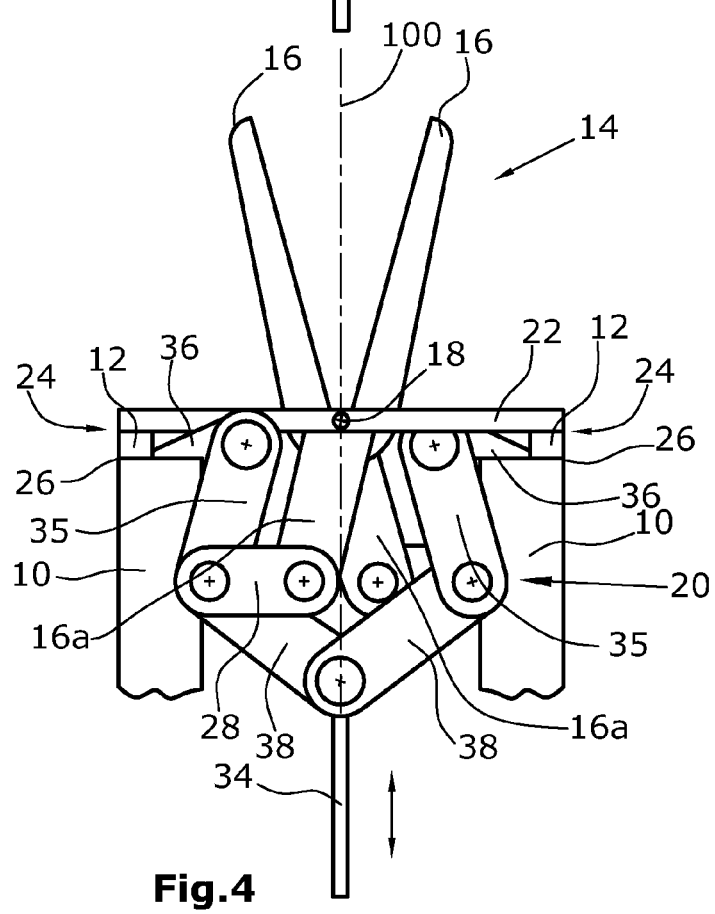

The following is a detailed explanation of the invention with reference to the accompanying Figures. In the Figures:

FIG. 1 is a schematic side elevational view of a robot structure according to the invention, with the grasping and/or cutting elements being closed, FIG. 2 is a schematic side elevational view of the robot structure shown in FIG. 1, with the grasping and/or cutting elements being opened, FIG. 3 is a schematic side elevational view of a second robot structure according to the invention, with the grasping and/or cutting elements being closed, and FIG. 4 is a schematic side elevational view of the robot structure shown in FIG. 3, with the grasping and/or cutting elements being opened.

FIGS. 1 and 2 schematically illustrate a first embodiment of a robot structure 1 of the present invention in side elevational view.

The robot structure 1 is formed by a first robot element 10 and a second robot element 14 movable relative thereto and comprising two grasping and/or cutting elements 16 adapted to be moved uniformly in opposed directions. FIG. 1 shows the robot structure 1 with the grasping and/or cutting elements 16 in the closed position, and FIG. 2 shows the same with the grasping and/or cutting elements 16 in the opened position.

The second robot element 14 is connected with the first robot element 10 by the grasping and/or cutting elements 16 being supported in a support element 22 through a hinge axis 18, the support element 22 being connected with the first robot element 10.

Two sensor elements 12 are arranged between the support element 22 and the first robot element 10, with the support element 22 being respectively connected with a sensitive end 24 of the sensor elements 12 and the first robot element being connected with a base element 26 of the sensor elements 12.

The sensor elements 12 measure the forces and/or moments caused by the grasping and/or cutting elements 16, which are transmitted to the sensitive end 24 of the sensor elements 12 via the hinge axis 18 and the support element 22.

The robot structure 1 comprises a force transmitting device 20 driving the grasping and/or cutting elements 16. For this purpose, the force transmitting device 20 comprises two identical drive mechanisms, each driving one of the grasping and/or cutting elements 16.

Hereinafter, only the drive mechanism for the right grasping and/or cutting element 16, as seen by the viewer, will be described. The drive mechanism of the left grasping and/or cutting element 16 is situated, hidden to the viewer, on the side of the force transmitting device 20 averted from the viewer and rotated by 180° around the central axis 100 of the robot structure 1.

The drive mechanism consists of a driving element 28 connected with the lower end 16*a* of the right grasping and/or cutting element 16. In order to generate a driving force exerted on the grasping and/or cutting element via the driving element 28, the force transmitting device 20 comprises a slotted guide device in the form of a guiding groove 30 in which a pin 32 of the driving element 28 is guided. In the embodiment illustrated in FIGS. 1 and 2, the guiding groove 30 is arranged under an angle with respect to the central axis 100 of the robot structure, the guiding groove 30 being inclined towards the movable robot element 14.

In the embodiment illustrated in FIGS. 1 and 2, the force transmitting device 20 is adapted to be driven via a pull/push rod 34, as illustrated in FIG. 1 by the double arrow. If the force transmitting device 20 is moved in a direction towards the movable robot element 14 by a pressure exerted via the pull/push rod 34, the driving element 28 is moved in a direction orthogonal to the central axis 100 of the robot structure 1, since the pin 32 of the driving element 28 is moved away from the central axis 100 by the guiding groove 30. Thereby, the driving element 28 exerts a pulling force on the lower end 16*a* of the right grasping and/or cutting element 16 so that the grasping and/or cutting element 16 is pulled to the open position. In doing so, a guiding element 35 in the form of a guiding lever causes the driving element 28 to remain oriented orthogonally with respect to the central axis 100 throughout the entire movement. Thereby, only force components of the driving forces are transmitted to the grasping and/or cutting element, which run in a direction orthogonal to the central axis 100. These forces are transmitted from the lower end of the grasping and/or cutting element to the hinge axis 28 and thus to the support element 22. Due to the fact that the drive mechanism for the left grasping and/or cutting element 16 is rotated by 180°, the driving elements 28 for the two grasping and/or cutting elements 16 extend in opposed directions so that also the forces exerted on the grasping and/or cutting elements by the driving elements 28 are opposed to each other. The corresponding driving forces are thus transmitted to the support element 22 via the hinge axis 18, but cancel each other due to their opposed directions. Thereby, the driving forces are not transmitted to the sensitive end 24 of the sensor elements 12 so that these are not included in the measurement of the grasping and/or contact forces.

In order to prevent the transmission of axially directed force components, which may be generated by friction of the pins 32 in the guiding grooves 30, for instance, to the driving elements 28 and thus to the support element 22, the guiding elements 35 are connected with the first robot element 10 and/or the base elements 26 of the sensor elements 12 through connecting elements 36. The guiding elements 35 and the connecting elements 36 absorb the force component in the axial direction and pass it to the first robot element 10 or the base elements 26. It is thereby prevented that force components generated by the force transmitting device 20 are sensed by the sensor elements 12 in the axial direction and are included in the measurement of the grasping and/or contact forces.

In a grasping or cutting process using the robot structure 1 of the present invention, the object grasped or treated exerts the grasping and/or contact force on the grasping and/or cutting elements 16, the grasping and/or cutting elements 16 transmitting the force as forces and/or moments on the hinge axis 18. From the hinge axis 18, these forces and/or moments are transmitted to the sensitive ends 24 of the sensor elements 12 via the support element 22, so that the sensor elements 12 can detect the forces and/or moments. From the values obtained, the actually existing grasping and/or contact forces can be calculated.

Due to the simple mechanical structure of the present robot structure 1 and very few moved parts, a sterilization of the robot structure 1 is particularly well possible, so that such a robot structure is particularly advantageous for the minimally invasive surgery.

In the embodiment illustrated in FIGS. 1 and 2, he driving elements 28 are designed as a rod and the guiding element 35 is designed as a guiding lever. Of course, it is also possible to guide the driving element 28 via a separate slotted guide device, for instance, such that the driving element 28 remains arranged orthogonally with respect to the central axis 100. In this case, the separate slotted guide device is preferably arranged in the connecting element.

The guiding function may also be realized by means of the already existing slotted guide device in the form of the guiding groove 30, e.g. by designing the pin 32 such that a rotation in the guiding groove 30 is prevented.

Instead of a pull/push rod 24, the force transmitting device 20 may also be driven by a spring-biased pull rod or a spring-biased push rod. It is also possible to drive the force transmitting device 20 via a spring-biased pull cable.

In the embodiment illustrated in FIGS. 1 and 2, the grasping and/or cutting elements 16 are opened by pushing the force transmitting device 20 towards the movable robot element 14. Of course, it is also possible that pulling the force transmitting device 20 in the opposite direction causes an opening of the grasping and/or cutting elements 16, due to the guiding grooves 30 being inclined in opposed directions.

The force transmission from the force transmitting device 20 to the driving elements 28 does not necessarily have to be performed via a slotted guide device. Of course, it is also possible to perform a force transmission in a different manner, while the driving elements 28 still remain arranged orthogonally with respect to the central axis 100 throughout the entire movement process.

FIGS. 3 and 4 illustrate a second embodiment of a robot structure of the present invention, with FIG. 3 showing the robot structure 1 with the grasping and/or cutting elements 16 closed and FIG. 4 showing the grasping and/or cutting elements 16 opened.

The robot structure 1 illustrated in FIGS. 3 and 4 comprises substantially the same functionally relevant parts as the first embodiment illustrated in FIGS. 1 and 2.

The robot structure 1 also consists of a first robot element 10 and a second robot element 14 movable with respect to the former and comprising two grasping and/or cutting elements 16 adapted to be moved uniformly in opposed directions. The grasping and/or cutting elements 16 are supported in a support element 22 via a hinge axis 18 connected with the first robot element 10. In this case, sensor elements 12 are arranged between the support element 22 and the first robot element 10 so that forces exerted on the support element 22 can be measured by the sensor elements 12, because the sensitive end 24 of the sensor elements 12 is connected with the support element 22.

The sensor elements 12 measure the forces and/or moments caused by grasping and/or contact forces to the grasping and/or cutting elements 16.

In order to move the grasping and/or cutting elements 16, the robot structure 1 comprises a force transmission device 22 that can be driven via a pull/push rod 34. In the embodiment illustrated in FIGS. 3 and 4, the force transmitting device 20 comprises two levers 38 respectively connected with the lower ends of the right and the left grasping and/or cutting element 16 via driving elements 28. When the pull rod 34 is moved, the levers 38 pivot apart, so that the lower ends 16a of the grasping and/or cutting elements 16 are pulled apart by the driving elements 28. Here, the levers 38 are designed such that the driving elements 28 are orientated orthogonally with respect to the central axis 100 throughout the entire movement process. Thus, only the force components of the driving forces that are directed orthogonally with respect to the central axis 100 are transmitted to the grasping and/or cutting elements 16. These forces are transmitted from the lower end 16a of the grasping and/or cutting elements to the hinge axis 18 and thus to the support element 22. Due to the fact that in the embodiment illustrated in FIGS. 3 and 4 the driving mechanism for the left grasping and/or cutting element 16 is rotated by 180° with respect to the driving mechanism for the right grasping and/or cutting element 16, forces are transmitted to the support element 22 in opposed directions, the forces thus canceling each other. Thus, the driving forces are not transmitted to the sensitive end 24 of the sensor elements 12.

In order to prevent force components from being transmitted to the driving elements and thus to the support element 22 in the axial direction of the robot structure 1, guiding elements 35 are connected with the first robot element 10 and/or the base elements 26 of the sensor elements 12 via connecting elements 36. The corresponding axial force components are transferred from the guiding elements 35 to the first robot element 10 and/or the base elements 26 of the sensor elements 12. Thereby, it can be prevented that axial force components generated by the force transmitting device 20 are detected by the sensor elements 12 and are included in the measurement of the grasping and/or contact forces.

The invention claimed is:

1. A robot structure for minimally invasive surgery, comprising:
    a first robot element and a second robot element that can be moved relative to the first robot element, said second robot element having two grasping and cutting elements which can be uniformly moved with respect to each other and which are connected to the first robot element via a hinge axis,
    a force transmitting device for moving the grasping and cutting elements of the second robot element and
    at least one sensor element comprising a sensitive end for receiving forces and moments that occur on the second robot element and comprising a base element that is fixed to the first robot element,
    wherein
    the hinge axis is supported in a support element in order to receive the forces and moments that are caused by grasping and contact forces on the grasping and cutting elements, and the support element is connected to the sensitive end of the at least one sensor element, and
    the force-transmitting device is connected to each of the grasping and cutting elements via a driving element, respectively, in order to initiate the movement, with the driving elements being disposed opposed to each other and in a substantially orthogonal manner with respect to a central axis of the robot structure and maintaining the substantially orthogonal manner with respect to the central axis during an entire moving process of the grasping and cutting elements,
    wherein a respective guiding element guides each of the driving elements such that the driving elements maintain the substantial orthogonal manner with respect to the central axis during the entire moving process of the grasping and cutting elements, wherein the guiding elements are each designed as guiding levers.

2. The robot structure of claim 1, wherein each driving element is designed as a rod.

3. The robot structure of claim 1, wherein the guiding elements are each connected with the first robot element and the base element of one of the at least one sensor elements via a connecting element.

4. The robot structure of claim 1, wherein the force transmitting device is adapted to be driven via a pull rod.

5. The robot structure of claim 1, wherein the force transmitting device is adapted to be driven via a pull rod or via a push rod, the pull rod or the push rod being spring-biased.

6. The robot structure of claim 1, wherein the force transmitting device is adapted to be driven via a pull cable, the pull cable being spring-biased.

7. The robot structure of claim 1, wherein the force transmitting device is adapted to be driven via a push rod.

8. A robot structure for minimally invasive surgery, comprising:
    a first robot element and a second robot element that can be moved relative to the first robot element, said second robot element having two grasping and cutting elements which can be uniformly moved with respect to each other and which are connected to the first robot element via a hinge axis,
    a force transmitting device for moving the grasping and cutting elements of the second robot element and
    at least one sensor element comprising a sensitive end for receiving forces and moments that occur on the second robot element and comprising a base element that is fixed to the first robot element,
    wherein the hinge axis is supported in a support element in order to receive the forces and moments that are caused by grasping and contact forces on the grasping and cutting elements, and the support element is connected to the sensitive end of the at least one sensor element, and
    the force-transmitting device is connected to each of the grasping and cutting elements via a driving element, respectively, in order to initiate the movement, with the driving elements being disposed opposed to each other and in a substantially orthogonal manner with respect to a central axis of the robot structure and maintaining the substantially orthogonal manner with respect to the central axis during an entire moving process of the grasping and cutting elements, wherein the force transmitting device drives each of the driving elements, respectively, via a slotted guide device, the driving elements comprising pins adapted to be guided in the slotted guide devices.

9. The robot structure of claim 8, wherein each driving element is designed as a rod.

10. The robot structure of claim 8, wherein the slotted guide devices each comprise a guiding groove arranged at an angle with respect to the central axis of the robot structure.

11. The robot structure of claim 8, wherein the force transmitting device is adapted to be driven via a pull rod.

12. The robot structure of claim 8, wherein the force transmitting device is adapted to be driven via a pull rod or via a push rod, the pull rod or the push rod being spring-biased.

13. The robot structure of claim 8, wherein the force transmitting device is adapted to be driven via a pull cable, the pull cable being spring-biased.

14. The robot structure of claim 8, wherein the force transmitting device is adapted to be driven via a push rod.

15. A robot structure for minimally invasive surgery, comprising:
- a first robot element and a second robot element that can be moved relative to the first robot element, said second robot element having two grasping and cutting elements which can be uniformly moved with respect to each other and which are connected to the first robot element via a hinge axis,
- a force transmitting device for moving the grasping and cutting elements of the second robot element and
- at least one sensor element comprising a sensitive end for receiving forces and moments that occur on the second robot element and comprising a base element that is fixed to the first robot element,
- wherein the hinge axis is supported in a support element in order to receive the forces and moments that are caused by grasping and contact forces on the grasping and cutting elements, and the support element is connected to the sensitive end of the at least one sensor element, and
- the force-transmitting device is connected to each of the grasping and cutting elements via a driving element, respectively, in order to initiate the movement, with the driving elements being disposed opposed to each other and in a substantially orthogonal manner with respect to a central axis of the robot structure and maintaining the substantially orthogonal manner with respect to the central axis during an entire moving process of the grasping and cutting elements, wherein the force transmitting device drives each of the driving elements via a lever, respectively.

16. The robot structure of claim 15, wherein each driving element is designed as a rod.

17. The robot structure of claim 15 wherein the force transmitting device is adapted to be driven via a pull rod.

18. The robot structure of claim 15, wherein the force transmitting device is adapted to be driven via a pull rod or via a push rod, the pull rod or the push rod being spring-biased.

19. The robot structure of claim 15, wherein the force transmitting device is adapted to be driven via a pull cable, the pull cable being spring-biased.

20. The robot structure of claim 15, wherein the force transmitting device is adapted to be driven via a push rod.

* * * * *